United States Patent [19]

Ratliff et al.

[11] Patent Number: 5,194,257

[45] Date of Patent: Mar. 16, 1993

[54] KIT AND METHOD FOR ADMINISTRATION OF BACILLUS CALMETTE-GUERIN FOR THE TREATMENT OF SUPERFICIAL BLADDER TUMORS

[75] Inventors: Timothy L. Ratliff; M'Liss A. Hudson; Julie K. Ritchey, all of St. Louis, Mo.

[73] Assignee: The Jewish Hospital of St. Louis, St. Louis, Mo.

[21] Appl. No.: 619,222

[22] Filed: Nov. 28, 1990

[51] Int. Cl.$^5$ .......................... C12N 1/20; A61K 35/74
[52] U.S. Cl. .................................. 424/93 K; 424/195.1
[58] Field of Search ....................................... 424/93 K Primary Examiner—David M. Naff
Assistant Examiner—Jean C. Witz
Attorney, Agent, or Firm—Senniger, Powers, Leavitt & Roedel

[57] ABSTRACT

Improved treatment of superficial bladder tumors through the administration by intravesical instillation of bacillus Calmette-Guerin is realized through the use of therapeutic composition comprising bacillus Calmette-Guerin (BCG) suspended in a 0.15 M sodium chloride solution containing a buffer to maintain the pH of the solution in the range 6.6 to 7.4, preferably 7.0. A kit and method are provided whereby such a composition may be employed to maximize intravesical attachment of BCG for improved efficacy.

7 Claims, 7 Drawing Sheets

KIT AND METHOD FOR ADMINISTRATION OF BACILLUS CALMETTE-GUERIN FOR THE TREATMENT OF SUPERFICIAL BLADDER TUMORS

BACKGROUND OF THE INVENTION

This invention relates to the administration of bacillus Calmette-Guerin in the treatment of superficial bladder tumors and, more particularly, to an improved kit and method for such administration through the use of an optimal diluent formulation.

Based upon the original work by Morales and associates, bacillus Calmette-Guerin (BCG) has been administered intravesically in the treatment and prophylaxis of recurrent bladder tumor. Morales et al., J. Urol., 116:180, 1976. In the initial study, 120 mg. BCG were reconstituted in 50 cc. normal saline and instilled via a catheter into the bladder. Patients were advised to retain the BCG solution for not less that 2 hours and additionally, patients received 5 mg. BCG intradermally. Treatments were given weekly for 6 weeks. This original regimen was arrived at arbitrarily and was amenable to modification as future data became available.

In subsequent studies, modification of this regimen focused on the elimination of the intradermal dose of BCG, increasing the number of weekly BCG treatments, introduction of maintenance BCG dosage schedules and introduction of other substrains of BCG. See Martinez-Pineiro, Bladder Tumors and Other Topics in Urological Oncology, Edited by M. Pavone-Macaluso et al., New York:Plenum Press, p. 175,1980; Brosman J. Urol., 36, 1985; Hudson et al., J. Urol., 138:295, 1987; Lamm et al., J. Urol., 135:272,1986; Brosman, J. Urol., 128:27, 1982; Lamm et al., J. Urol., 128:931, 1982; Lamm, J. Urol., 134:40, 1985; Mori et al. Urol. Int., 41:254,1986; and Kelley et al., J. Urol., 134:48, 1985. In these studies, little attention has been paid to the actual administration conditions of the individual doses of BCG. Diluents reported in the literature for the reconstitution of lyophilized BCG preparations include normal saline, phosphate buffered saline or sterile water. The retention time for each BCG dose in these prior studies has been 30 minutes to 2 hours.

Recent studies have suggested that an initial requisite step in mediating the antitumor effect of BCG is attachment of BCG organisms to matrix fibronectin at sites of urothelial disruption. Ratliff et al., J. Urol., 139:3:410, 1988. Fibronectin is a glycoprotein with a molecular weight of 440 kD. It is found in a soluble form in plasma and other body fluids, and in an insoluble (matrix) form on cell surfaces, basement membranes and extracellular matrixes. Mosher, Prog. Hemat. Thromb., 5:111,1980. It has been demonstrated that pretreatment of BCG with soluble fibronectin prevents the binding of BCG to matrix fibronectin exposed on the murine bladder wall after mucosal disruption. Ratliff et al., supra. The inhibition of intravesical BCG attachment resulted in the loss of antitumor activity. Ratliff et al., Cancer Res. 47:1762, 1987.

There has been a continuing need to determine the optimal composition and physical conditions for the diluent in which the BCG is suspended and the interval that BCG is exposed to fibronectin so as to maximize the efficacy of BCG administration.

SUMMARY OF THE INVENTION

Among the several objects of the invention may be noted the provision of an improved kit and method for the administration of BCG; the provision of such an improved method in which the BCG is administered in the form of a therapeutic composition containing BCG suspended in a 0.15 M sodium chloride solution containing a buffer to maintain the pH of the solution within the optimal range; and the provision of such an improved kit and method which maximize intravesical attachment of BCG in the treatment of superficial bladder tumors. Other objects and features will be in part apparent and in part pointed out hereinafter.

Briefly, the present invention is directed to a kit for use in the in vivo treatment of superficial bladder tumors through the administration by intravesical instillation of BCG comprising:

(a) a dosage amount of BCG in lyophilized form; and
(b) a 0.15 M sodium chloride solution containing a buffer to maintain the pH of the solution in the range 6.6 to 7.4.

The invention also includes the method for the treatment of superficial bladder tumors in a mammal comprising administering to the mammal a therapeutic composition comprising BCG suspended in a 0.15 M sodium chloride solution containing a buffer to maintain the pH of the solution in the range 6.6 to 7.4.

DESCRIPTION OF THE PREFERRED EMBODIMENTS

Figure 1:
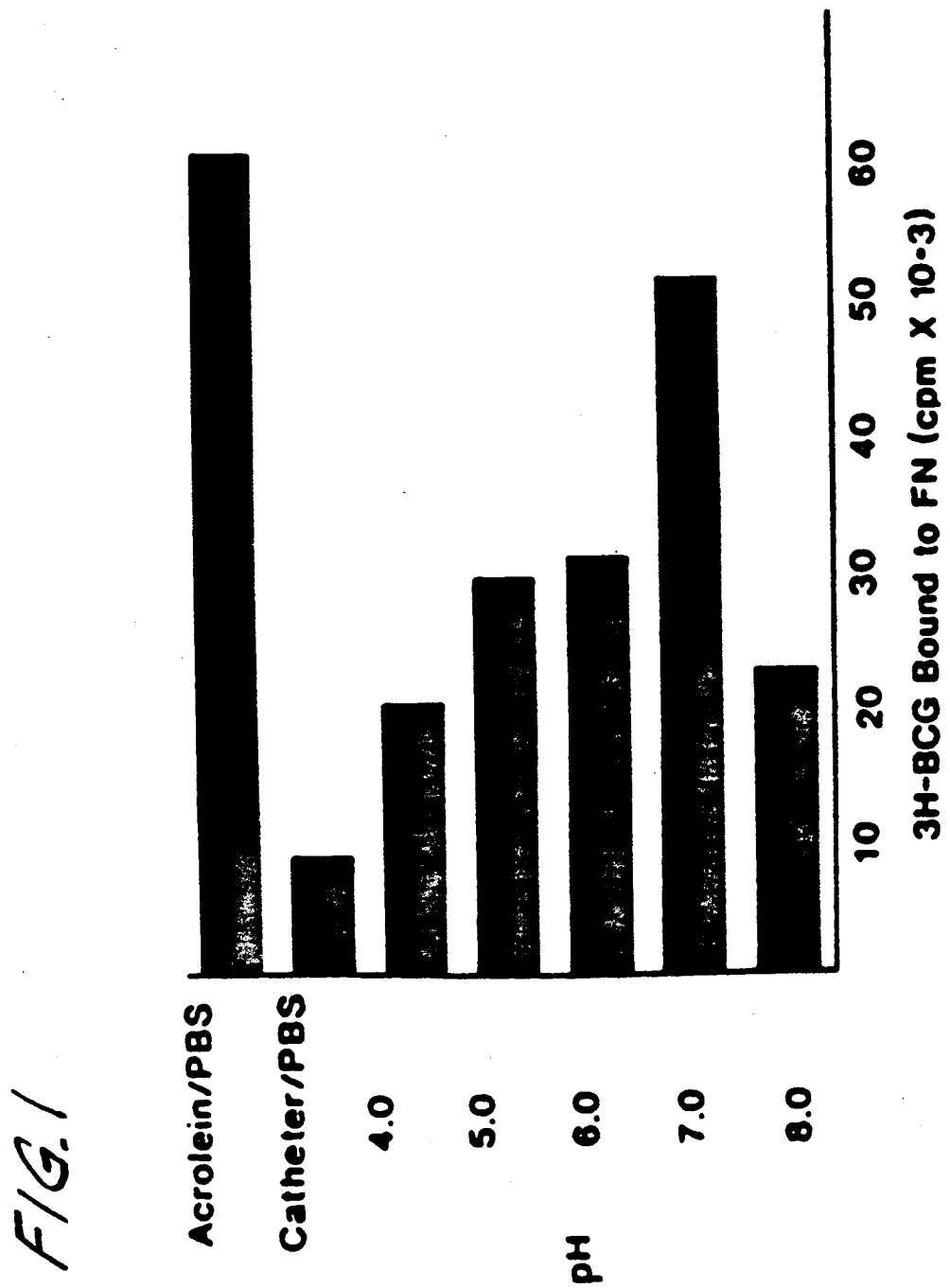
FIG. 1 is a graph showing the effect of diluent pH on fibronectin-BCG binding in vivo.

In accordance with the present invention, it has now been found that the optimal diluent composition for maximizing BCG attachment to matrix fibronectin while minimizing soluble fibronectin-BCG binding is comprised of a 0.15 M sodium chloride solution containing a buffer to maintain the pH at approximately 7.0 or within the narrow range 6.6 to 7.4, with the optimal length of exposure of BCG to fibronectin being approximately 2 hours. While normal saline (0.15 M) has been used in the past as a diluent for BCG, it has remained unrecognized that unless the diluent is maintained at a pH of approximately 7.0 (or within the narrow range 6.6 to 7.4), optimal results will not be attained. Normal saline solutions are susceptible to pH variations, as by absorption of carbon dioxide from the atmosphere, and we have found that it is critical to maintain the pH of the 0.15 M sodium chloride at a pH of approximately 7.0 in order to maximize matrix fibronectin-BCG binding while minimizing soluble fibronectin-BCG binding so that maximal fibronectin-BCG binding occurs at the disrupted urothelial surface. Through the present invention, it has been found that such optimal results can be attained by buffering the 0.15 M sodium chloride solution with a buffer effective to maintain the pH of the solution at approximately 7.0 or within the narrow range 6.6 to 7.4.

As demonstrated by the results of the experimental in vivo studies set forth hereinafter, maximal BCG-binding to chemically injured murine bladders occurs at pH 7.0 and at a diluent sodium chloride concentration of 0.15 M, these results being obtained by buffering the sodium chloride solution with various buffers to maintain the diluent pH at the optimal 7.0. These in vivo studies also demonstrate maximal BCG-fibronectin binding at 2 hours retention time. Thus, the particular combination of physical conditions and diluent composition afforded by the present invention provides the optimal efficacy for BCG therapy against superficial bladder tumors.

In accordance with the invention, as shown by the results set forth hereinafter, various buffers may be utilized to maintain the pH of the 0.15 M sodium chloride diluent solution at approximately 7.0. These include the following buffers: phosphate, Tris [Tris(hydroxymethyl)aminomethane], TES(N-tris[hydroxymethyl]methyl-2-aminoethanesulfonic acid), BES (N,N,-bis[2-hydroxyethyl]-2-aminoethanesulfonic acid), MOPS(3-(N-morpholino)propanesulfonic acid), MOPSO(3-(N-morpholino)-2-hydroxy-propanesulfonic acid), and HEPES((N-[2-hydroxyethyl]piperazine-N'-[2ethanesulfonic acid]). Other buffers known to those skilled in the art may also be used in the practice of the invention to maintain the pH of the sodium chloride diluent solution at a pH of approximately 7.0.

In the practice of the invention, a kit is provided which contains a dosage of BCG and a 0.15 M sodium chloride solution containing a buffer to maintain the pH of the solution at a pH of approximately 7.0. Typically, the dosage of BCG is constituted by a vial containing 120 mg. BCG in lyophilized form which is reconstituted in 50 ml. of the aforementioned buffered 0.15 M sodium chloride solution for administration by intravesical instillation to a patient as known to the art. The reconstituted BCG composition provides, for example, $2.7 \times 10^8$ colony-forming units of BCG. The kit and administration method of the invention thus provide optimal efficacy for BCG therapy.

The following examples illustrate the practice of the invention.

EXAMPLE 1

Bacteria. Lyophilized bacillus Calmette-Guerin (BCG), Pasteur substrain at 120 mg. per vial, was used in the following studies. Before attachment assays were performed, BCG was radiolabeled with tritiated ($^3$H) uracil as described.

Radiolabeling of bacteria. A 120 mg. ampule of BCG was cultured for 5 to 7 days in 100 ml. Youman's medium at 37° C. in 5% carbon dioxide. Youman's medium has the following composition:

| Asparagine | 5.0 g. |
| Monopotassium phosphate | 5.0 g. |
| Potassium sulfate | 0.5 g. |
| Magnesium citrate | 1.5 g. |
| L-glutamic acid | 19.0 g |

-continued

| Glycerine (glycerol) | 20.0 ml. |
| Bovine serum albumin | 5.0 g. |
| Distilled water q.s. to | 1000 ml. |

Bacteria were washed in phosphate buffered saline and resuspended in 10 ml. RPMI-1640 medium supplemented with 0.2% L-glutamine, 0.2% asparagine and 0.5ferric ammonium citrate $^3$H-Uracil (10 μCi./ml, American Radiolabelled Chemicals, St. Louis, Miss.) was added to the culture and incubated for hours at 37° C. in 5% carbon dioxide. The bacteria then were washed twice in phosphate buffered saline and resuspended in diluents of varying pH or salt concentration, or phosphate buffered saline for time experiments. The number of organisms was determined by measuring optical density at a wavelength of 595 nM. and comparing it to a standard curve for quantitating colony-forming units from optical densities.

Diluents. To prepare diluents for the matrix fibronectin binding studies described below with a pH level of 4 to 6, solutions of 0.1;4 2[N-morpholino]ethanesulfonic acid buffer plus 0.15 M sodium chloride were titrated to the appropriate pH with sodium hydroxide. To prepare diluents with a pH level of 7 or 8, solutions of 0.1 M Tris buffer plus 0.15 M sodium chloride were titrated to the appropriate pH with hydrochloric acid. To prepare diluents for the soluble fibronectin binding studies described below with a pH of 3 to 6, 0.1 M ammonium acetate buffer without sodium chloride was used, while 0.1 M Tris buffer without salt was used for pH 7 to 10.

Purification of fibronectin. Human plasma fibronectin was purified as previously described (Pommier et al., J. Exp. Med., 57 1844, 1983). Briefly, 10% polyethylene glycol 3350 precipitate from ethylenediaminetetraacetic acid (EDTA), benzamidine and phenylmethylsulfonyl fluoride-treated plasma were resuspended in a buffer of 150 nM sodium chloride, 50 mM monobasic/ dibasic potassium phosphate and 10 nM EDTA, pH 7.4. This plasma fraction then was absorbed by passage over gelatin-Sepharose 4B (Pharmacia Fine Chemicals, Piscataway, N.J,) and the fibronectin was purified by elution from gelatin-Sepharose with 1 M arginine. All buffers used for chromatography and elution contained 5 nM benzamidine, 1 nM phenylmethylsulfonyl fluoride and/or 0.5 nM paranitrophenyl-para-guanido benzoate to inhibit serum proteases. The purified fibronectin showed a single band on immunoelectrophoresis versus anti-whole human serum, and a single major band at 440,000 D. on sodium dodecylsulfatepolyacrylamide gel electrophoresis. Upon reduction of disulfide bonds, sodium dodecylsulfate-polyacrylamide gel electrophoresis revealed a closely spaced doublet, as has been reported previously for human plasma fibronectin. Antibodies raised against this fibronectin preparation in rabbits and goats gave a specific response to fibronectin on immunoelectrophoresis and Ouchterlony double diffusion against whole human plasma.

Radiolabeling of vibronectin. Purified human fibronectin (1.5 mg/ml.) was labeled for 15 minutes with 1 mCi$^{125}$ iodine ($^{125}$I) sodium (Amersham Corp. Arlington Heights, Ill.) in a siliconized test tube. The labeled $^{125}$I-fibronectin was separated from unbound $^{125}$I by chromatography on a 10 ml. volume G25 Sephadex column as described by Pommier and associates (J. Exp. Med. 159:137, 1984). The specific activity of the $^{125}$I- fibronectin was routinely between $10^6$ and $10^7$ counts per minute per μg. fibronectin.

In vitro soluble fibronectin binding assay. The binding assay was performed as described by Proctor and associates (J. Biol. Chem., 257:14788, 1982). Briefly, 6 μg. $^{125}$I-fibronectin were added to 1.5 ml. volume microfuge tubes (Eppendorf, Westbury, N.Y.) precoated for 2 hours with 1 ml. human serum albumin (1 mg./ml.) containing $7\times10^8$ colony-forming units/ml.BCG suspended in 1 ml. 0.1 M Tris buffer, pH 6. The $^{125}$I-fibronectin was mixed with either 300 μl. unlabeled fibronectin (1 mg./ml.) or 300 μl. of appropriate buffer to determine nonspecific and total binding, respectively. The reaction mixtures were allowed to incubate for 1 hour at 22° C. After incubation, the microfuge tubes containing the reaction mixtures were centrifuged at 10,000 times gravity for 3 minutes in a Beckman Microfuge B. The supernatant containing free radiolabeled fibronectin was removed. The microfuge tubes were sliced and pellets containing radiolabeled fibronectin bound to BCG were analyzed for radioactivity. Control experiments using $^{125}$I-fibronectin without bacteria produced background counts of less than 500 per minute.

In vitro matrix fibronectin binding assays. Culture wells incubated with 1 fibronectin for 1 hour. Control wells were coated with 120 μg. human serum albumin for 1 hour. Wells were washed with phosphate buffered saline and then $2.5\times10^6$ colony-forming units of BCG solutions were added to each well. Wells were incubated at 37° C. and 5% carbon dioxide for 2 hours for the pH and salt concentration assays. Time assays were incubated for 30 minutes, and 1 to 4 hours. Each replicate was assayed in quadruplicate. Wells were washed twice in phosphate buffered saline and then transferred to vials, and attached bacteria were quantified by liquid scintillation counting.

In vivo adherence of BCG. Intravesical BCG instillation was performed as described previously (Ratliff et al., Cancer Res., 47:1762, 1987). Briefly, mice ($C_3$H/HEN, Charles River) were anesthetized with sodium phenobarbitol given intraperitoneally (0.05 mg./gm.animal weight). Anesthetized mice were catheterized with a 24 gauge polytetrafluoroethylene (Teflon) sheath. Chemical bladder injury (previously shown to induce fibronectin-dependent BCG attachment) was induced by intravesical instillation of 0.1 ml. dilute acrolein (1:160 dilution with phosphate buffered saline) for 30 minutes. Control mice received 0.1 ml. phosphate buffered saline intravesically for 30 minutes. These solutions then were expressed by the Crede manuveur and the bladder was washed with 0.1 ml. phosphate buffered saline. Appropriate BCG solutions containing $10^7$ colony-forming units per 0.1 ml. were instilled intravesically for 30 minutes for pH and salt concentration studies. Time studies were performed for 30 minutes, and 1 to 4 hours. The mice were sacrificed, and the bladder was removed surgically and washed in phosphate buffered saline. The bladder was minced in 10 ml. Scintiverse and adherence was determined by liquid scintillation counting.

Statistical analysis. Statistical significance was determined by a paired t test. Nonspecific fibronectin binding was defined as binding to controls. Specific fibronectin binding was defined as total counts per minute of the fibronectin group minus total counts per minute of the control group. Colony-forming units bound was defined as specific fibronectin-binding divided by the total counts per minute per colony-forming units.

The results may be summarized as follows:
Effect of diluent pH On BCG-fibronectin binding.
In vitro soluble fibronectin binding assays indicated that the specific binding of $^{125}$I-fibronectin to BCG occurred within a pH of 3 to 6, with minimal, $^{125}$I-fibronectin binding at a pH of 7 or higher. Similarly, in vitro matrix fibronectin binding assays indicated that maximal specific binding of $^3$H-BCG to fibronectin-coated surfaces occurs at pH 5 to 6. Studies then were performed to assess the influence of diluent pH in intravesical BCG attachment. In vivo studies demonstrated that maximal $^3$H-BCG binding to chemically injured murine bladders occurs at pH 7 (see FIG. 1).

Figure 2:
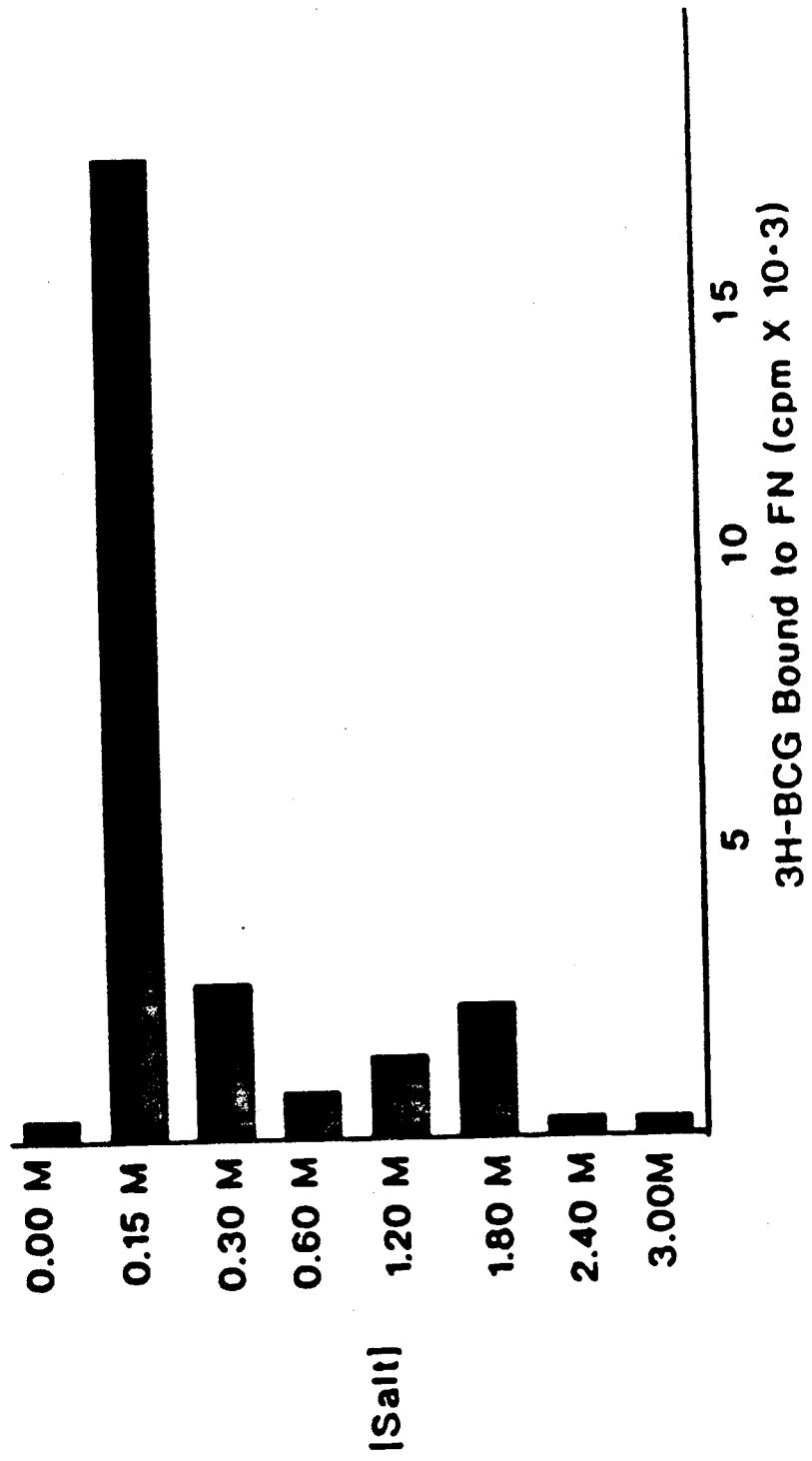
FIG. 2 is a graph showing the effect of diluent sodium chloride concentration on matrix fibronectin-BCG binding in vitro.
Figure 3:
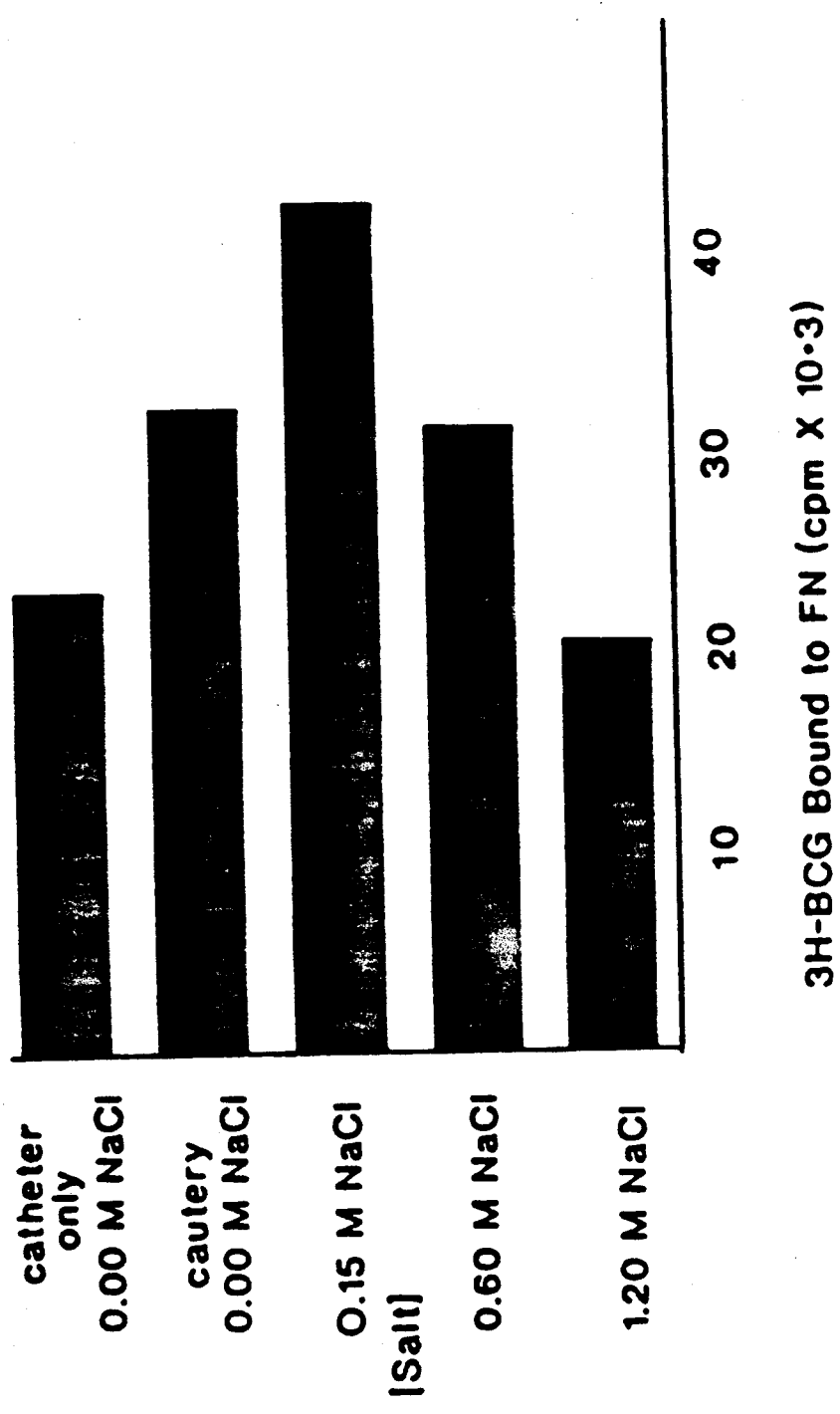
FIG. 3 is a graph showing the effect of diluent sodium chloride concentration on fibronectin-BCG binding in vivo.
Figure 4:
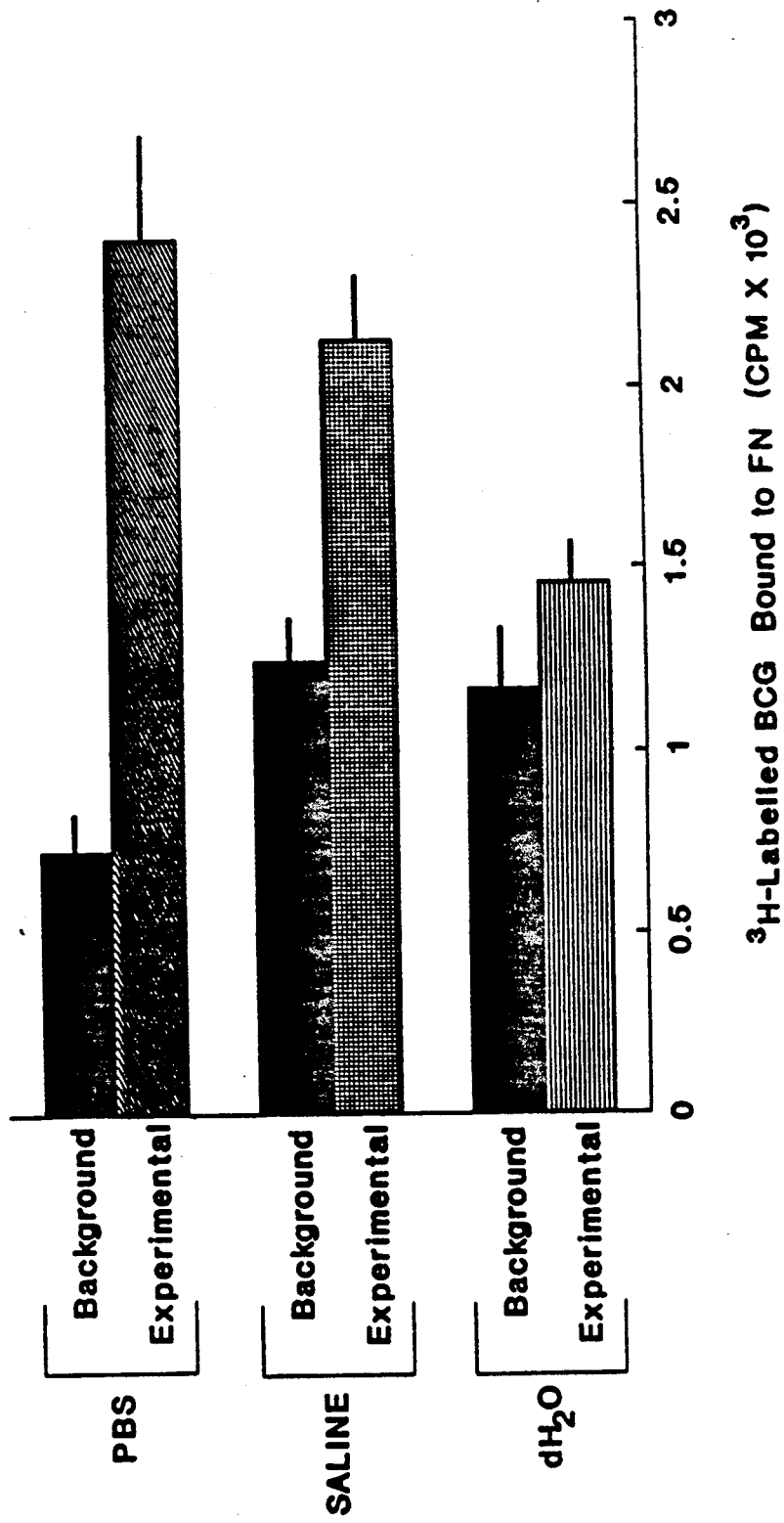
FIG. 4 is a graph showing the effect of phosphate buffered saline, plain saline and distilled water on BCG attachment.
Figure 5:
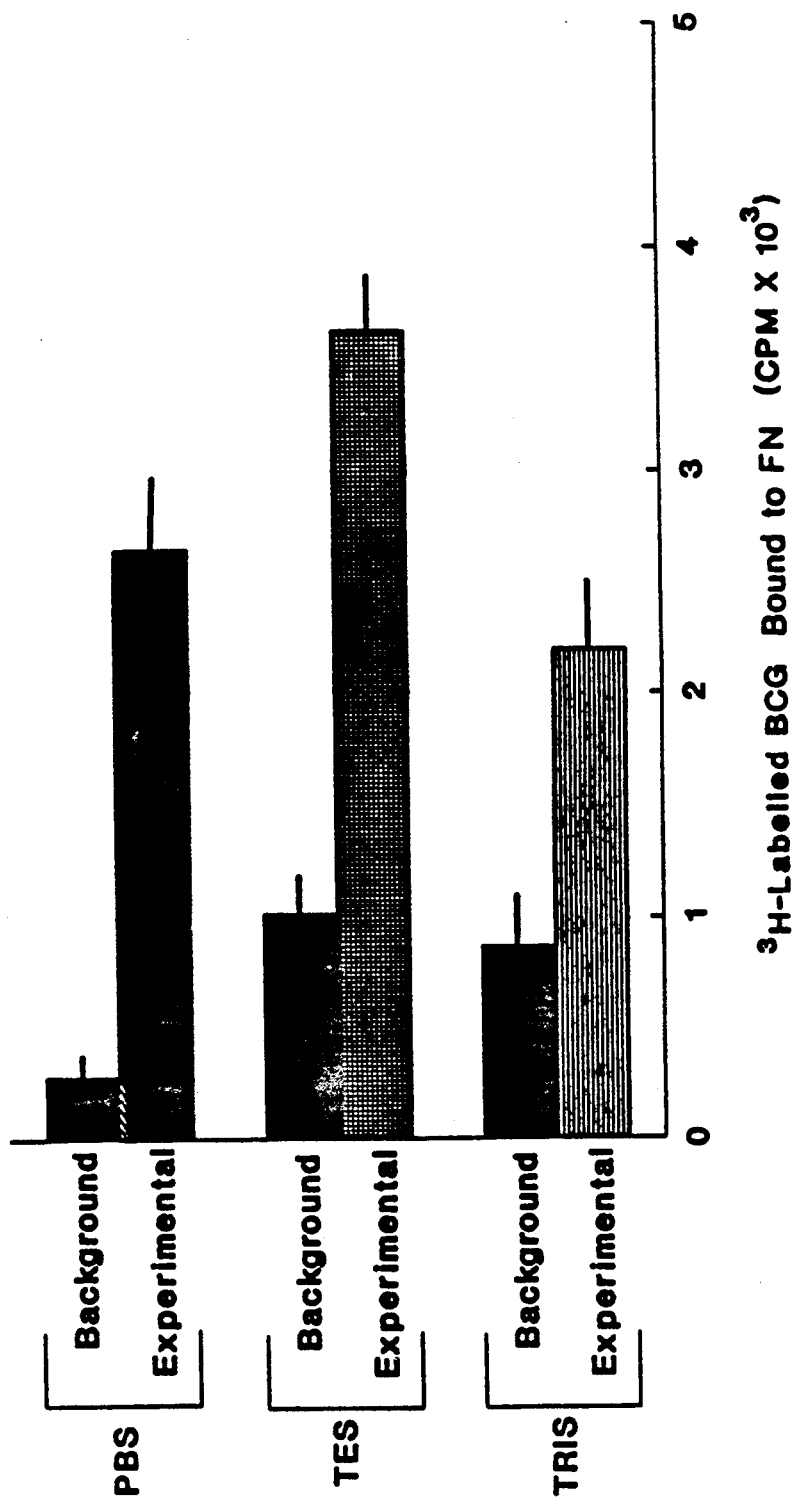
FIG. 5 is a graph showing the effect of three different buffers on BCG attachment.
Figure 6:
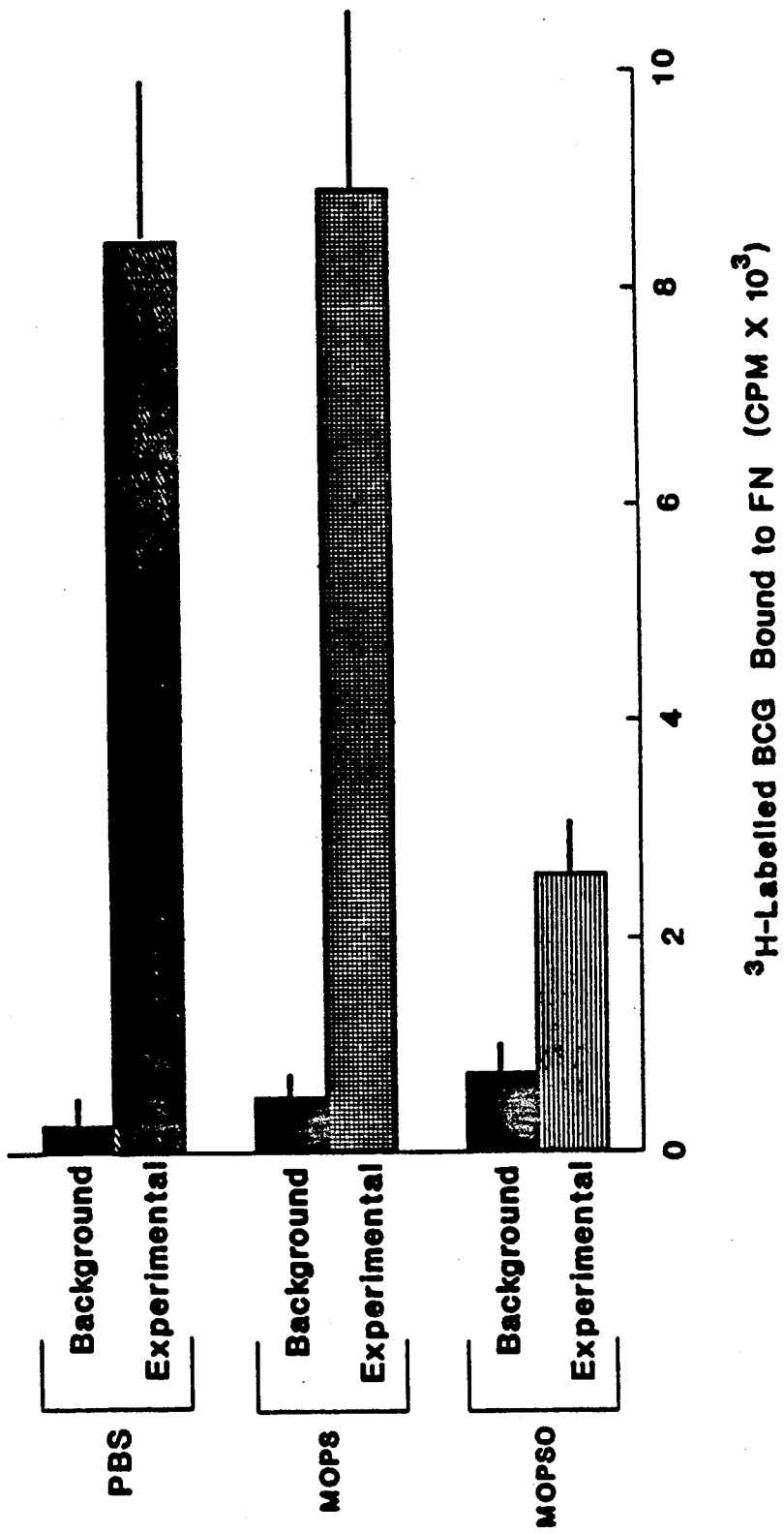
FIG. 6 is a graph showing the effect of three different buffers on BCG attachment.
Figure 7:
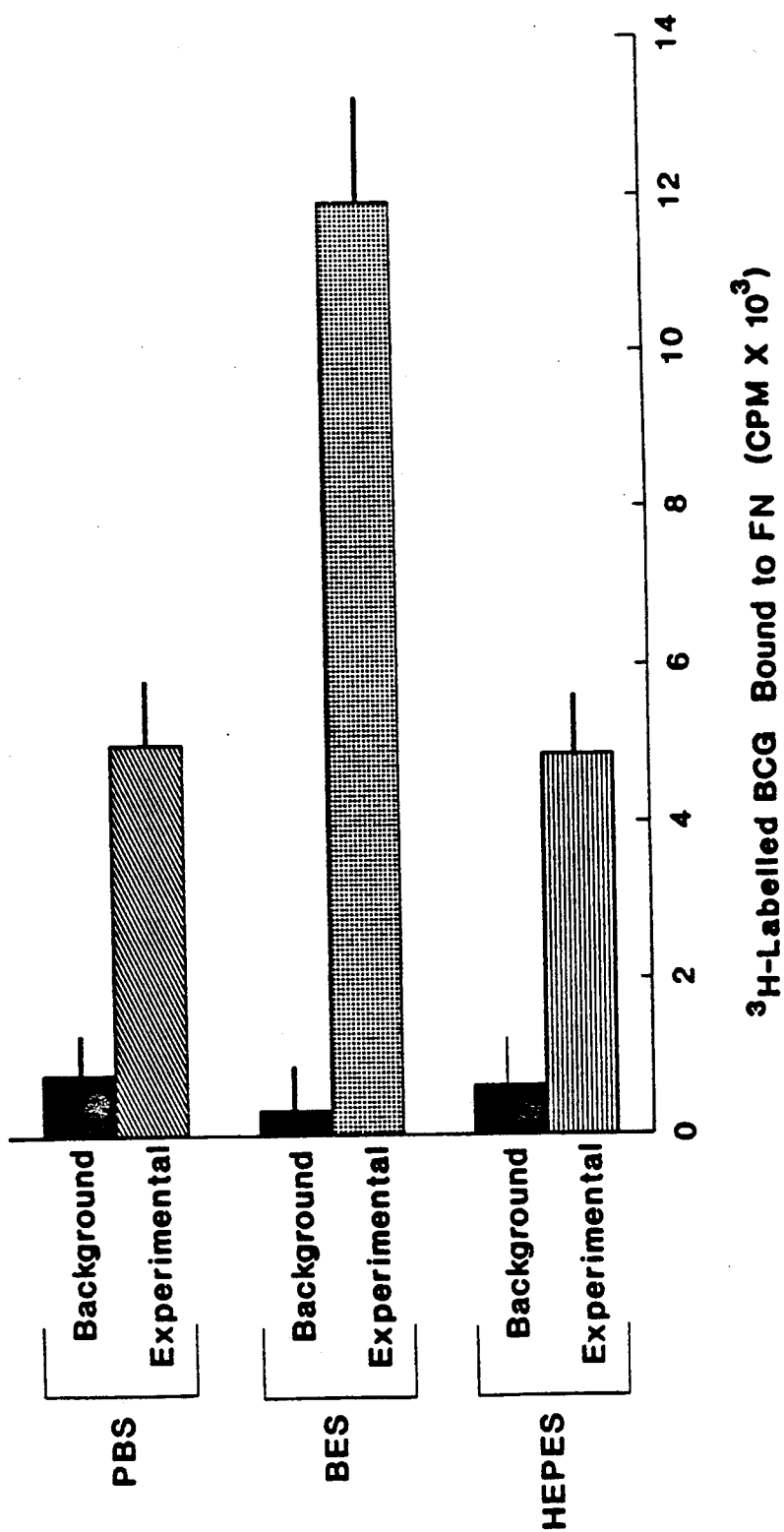
FIG. 7 is a graph showing the effect of three different buffers on BCG attachment.

Effect of diluent salt concentration on BCG-fibronectin binding. In vitro soluble fibronectin assays show that the presence of sodium chloride in the diluent at concentrations of 0.15 to 3.0 M inhibits $^{125}$I-fibronectin binding to BCG compared to a salt-free diluent. In contrast, in vitro matrix fibronectin binding assays show that $^3$H-BCG binding is enhanced in the presence of 0.15 M sodium chloride (normal saline) compared to hypertonic saline diluent or salt-free diluent (see FIG. 2). In vivo studies performed to determine the influence of sodium chloride concentration on intravesical BCG attachment also demonstrated maximal $^3$H-BCG binding at a diluent salt concentration equal to 0.15 M sodium chloride (see FIG. 3).

Effect of interval on BCG-fibronectin binding. In vitro soluble fibronectin binding assays showed that $^{125}$I-fibronectin-BCG binding reached equilibrium in less than 3 minutes and that less than 20% of the bound fibronectin was released during a 24-hour period. In vitro matrix fibronectin binding assay s demonstrated maximal specific $^3$H-BCG-fibronectin binding at 2 hours with a gradual decrease in binding during the subsequent 2 hours. In vivo studies also demonstrated maximal $^3$H-BCG-fibronectin binding at 2 hours with a gradual decrease in binding thereafter.

EXAMPLE 2

The procedure described in Example 1 for in vivo adherence of BCG was repeated using a number of buffered sodium chloride preparations. In each instance, a 0.15 M solution of sodium chloride was employed, the buffer at a concentration of 0.1 M was added and the buffered diluents were equilibrated to a pH of 7.0 at room temperature. The following buffers were used:

Phosphate
Tris [Tris(hydroxymethyl)aminomethane]
TES (N-tris[hydroxymethyl]methyl-2-aminoethanesulfonic acid)
BES (N,N, -bis[2-hydroxyethyl]-2-aminoethanesulfonic acid)
MOPS (3-(N-morpholino)propanesulfonic acid)
MOPSO(3-(N-morpholino)-2-hydroxy-propanesulfonic acid)
HEPES (N-[2-hydroxyethyl]piperazine-N-[2-ethanesulfonic acid])

The sodium salt of each of the buffers listed was employed. Attachment studies were also run with saline (0.15 M) and distilled water.

The results are shown in FIGS. 4-7. With each of the above-noted buffers in a 0.15 M sodium chloride solution buffered to a pH of 7.0, attachment was improved and the results were statistically significant compared to the background control. Distilled water was shown to be a poor diluent while 0.15 M saline functioned poorly, in both cases the results not being statistically significant when compared to the background control. Each of the bars in FIGS. 4-7 represents a group of 10 mice.

In view of the above, it will be seen that the several objects of the invention are achieved and other advantageous results attained.

As various changes could be made in the above methods and products without departing from the scope of the invention, it is intended that all matter contained in the above description shall be interpreted as illustrative and not in a limiting sense.

What is claimed is:

1. A kit for use in the in vivo treatment of superficial bladder tumors through the administration by intravesical instillation of bacillus Calmette-Guerin comprising:
   (a) a dosage amount of bacillus Calmette-Guerin in lyophilized form; and
   (b) a 0.15 M sodium chloride solution containing a buffer to maintain the pH of said solution within the range 6.6 to 7.4.

2. A kit as set forth in claim 1 wherein said sodium chloride solution is maintained at a pH of approximately 7.0.

3. A kit as set forth in claim 1 wherein said buffer is selected from the group consisting of phosphate, Tris (hydroxymethyl)aminomethane, N-tris[hydroxymethyl]-methyl-2-aminoethanesulfonic acid, N,N-bis[2-hydroxyethyl]-2-aminoethanesulfonic acid, 3-(N-morpholino)propanesulfonic acid, 3-(N-morpholino)-2-hydroxy-propanesulfonic acid, and N-[2-hydroxyethyl]piperazine-N[2-ethanesulfonic acid].

4. A method for the treatment of superficial bladder tumors in a mammal which comprises administering to said mammal a therapeutic composition comprising bacillus Calmette-Guerin suspended in a 0.15 M sodium chloride solution containing a buffer to maintain the pH of said solution in the range 6.6 to 7.4.

5. A method as set forth in claim 4 wherein said sodium chloride solution is maintained at a pH of approximately 7.0.

6. A method as set forth in claim 4 wherein said buffer is selected from the group consisting of phosphate, Tris (hydroxymethyl)aminomethane, N-tris[hydroxymethyl]methyl-2-aminoethanesulfonic acid, N,N-bis[2-hydroxyethyl]-2-aminoethanesulfonic acid, 3-(N-morpholino)propanesulfonic acid, 3-(N-morpholino)-2-hydroxy-propanesulfonic acid, and N-[2-hydroxyethyl]piperazine-N[2-ethanesulfonic acid].

7. A method as set forth in claim 4 wherein said treatment is continued for a period of approximately 2 hours.

* * * * *